(12) United States Patent
Patti

(10) Patent No.: US 10,176,339 B2
(45) Date of Patent: Jan. 8, 2019

(54) METHOD AND APPARATUS FOR ANONYMIZED MEDICAL DATA ANALYSIS

(71) Applicant: Jordan Patti, Los Angeles, CA (US)

(72) Inventor: Jordan Patti, Los Angeles, CA (US)

( * ) Notice: Subject to any disclaimer, the term of this patent is extended or adjusted under 35 U.S.C. 154(b) by 67 days.

(21) Appl. No.: 15/012,828

(22) Filed: Feb. 1, 2016

(65) Prior Publication Data

US 2016/0224805 A1   Aug. 4, 2016

Related U.S. Application Data

(60) Provisional application No. 62/110,484, filed on Jan. 31, 2015.

(51) Int. Cl.
*G06F 7/04* (2006.01)
*G06F 21/62* (2013.01)
*G06F 19/00* (2018.01)

(52) U.S. Cl.
CPC ........ *G06F 21/6254* (2013.01); *G06F 19/321* (2013.01)

(58) Field of Classification Search
CPC ....... A61B 5/026; A61B 5/0263; A61B 5/055; A61B 5/415; A61B 5/416; A61B 5/4848; A61B 5/7271; A61B 6/501; A61B 6/507; G06F 17/10; G06F 17/11; G06F 19/12; G06F 19/24; G06F 19/321; G06F 21/6254
See application file for complete search history.

(56) References Cited

U.S. PATENT DOCUMENTS

| 2006/0074983 | A1* | 4/2006 | Jones | G06F 19/323 |
| 2009/0234237 | A1* | 9/2009 | Ross | A61B 5/026 600/504 |
| 2011/0153351 | A1* | 6/2011 | Vesper | G06Q 10/10 705/2 |
| 2015/0223057 | A1* | 8/2015 | Dellarciprete | H04W 12/02 455/410 |

* cited by examiner

*Primary Examiner* — Abiy Getachew
(74) *Attorney, Agent, or Firm* — Che-Yang Chen; Law Offices of Scott Warmuth

(57) ABSTRACT

A data processing system may include a local computing device to receive medical data including a patient's protected health information (PHI) and at least one medical image associated with the patient; an anonymizing device to separate the PHI with the medical image; an image processing unit to analyze the medical image; and a processed results managing (PRM) unit configured to recognize and link analyzed results of the medical image to the corresponding patient's PHI, and combine the analyzed results and the patient's PHI to generate an analysis report. The present invention is advantageous because it allows medical images to be analyzed off-site while minimizing the risk of compromising the patient's PHI. Furthermore, the anonymized medical analysis can be used to guide and improve medical treatment especially during a medical procedure.

8 Claims, 9 Drawing Sheets

METHOD AND APPARATUS FOR ANONYMIZED MEDICAL DATA ANALYSIS

CROSS REFERENCE TO RELATED APPLICATIONS

This application claims priority under 35 U.S.C. § 119 (e) to U.S. Provisional Patent Application Ser. No. 62/110,484, filed on Jan. 31, 2015, the entire contents of which are hereby incorporated by reference.

FIELD OF THE INVENTION

The present invention relates to a medical data processing system, and more particularly to an image processing system configured to process anonymized medical images.

BACKGROUND OF THE INVENTION

Medical imaging can be used to diagnose illness and plan or evaluate treatment. Medical images are acquired through a variety of technologies, such as X-ray, magnetic resonance imaging (MRI), and ultrasound. The images produced reveal a patient's internal anatomy and physiological processes. Some techniques produce three-dimensional (3D) images, such as computerized axial tomography (X-ray CT or CT scan). Other techniques instead acquire a sequence of two-dimensional (2D) images, such as 2D digital subtraction angiography (DSA). Time-resolved 3D images are often referred to as four-dimensional (4D) images.

Specialized scanners are used to acquire raw data unique to a particular technique, which is then converted into images that can be viewed by a physician. Computational methods can be applied to further process, analyze, or enhance medical images and provide physiological information that is otherwise not evident in the basic medical images, such as blood flow or tissue material properties. In many cases, simple image processing tools are integrated into the software used for viewing medical images, providing functions such as the ability to render a set of images in 3D. More advanced image analysis is sometimes available on dedicated workstation computers which provide the necessary hardware and software. Or, advanced image analysis may be set up with a client-server configuration, whereby a server provides additional computational power for image processing and may be shared by multiple clients.

For several reasons, it may be preferable to perform computational image analysis at a different location from the hospital or clinic where images are acquired. For instance, the computational requirements may be high and impractical to physically locate at the site of image acquisition. The analysis methods may be proprietary and not available/licensed for use at the site. Analyzing images on site may complicate an already hectic operating environment. Or, it may simply be more cost-effective to have the images processed at a different location, possibly by a third party. As a result, it is better for images to be sent elsewhere for analysis.

Medical images, most often in the DICOM format, contain a great deal of patient-identifying information, and legislation, as well as best practices mandate maintaining patient privacy. Also, in the case of clinical trials, it may be necessary to hide information which may lead to bias (blinded experiments). In large part due to privacy concerns, it is currently uncommon for images to be sent to remote locations for computational analysis, especially in the midst of medical procedures. However, if images could be sent to remote locations, a powerful computer could be used to rapidly perform computationally-intensive image analysis during a medical procedure, providing valuable information to guide and improve treatment.

Therefore, there remains a need for a new and improved medical imaging process to allow medical images to be analyzed off-site while minimizing the risk of compromising patient-identifying information.

SUMMARY OF THE INVENTION

It is an object of the present invention to provide a method and system to process anonymized medical data.

It is another object of the present invention to provide a method and system to allow anonymized medical images to be analyzed off-site while minimizing the risk of compromising patient-identifying information.

It is a further object of the present invention to provide a medical analysis which can be used to guide and improve medical treatment especially during a medical procedure.

In one aspect, a method for processing medical data may include steps of receiving medical data from a local device, the medical data including a patient's protected health information (PHI) and at least one medical image associated with the patient; separating the PHI and the medical image; processing the medical image; and generating a medical data analysis including the PHI with processed results of the medical image.

In one embodiment, the step of separating the PHI and the medical image can be conducted on the local device. In another embodiment, the step of processing the medical image may further include steps of transmitting the medical image to a remote computing device, assigning an identifier to the medical image, analyzing the medical image, and transmitting results of the analyzed medical image to the local device. It is important to note that step of separating the PHI and the medical image is the step of anonymization, which is performed prior to the medical images leaving the local device. This is necessary to prevent the exposure of PHI to a remote computer system. In some embodiments, the step of analyzing the medical image can also be performed in the local computing device.

In an exemplary embodiment, the medical image and results of the analyzed medical image can be transmitted electronically, such as through the Internet, a private network, or intranet. However, in some cases, such as limited network connectivity, it may be preferable for the data to be transferred physically, such as a DVD or hard disk drive sent through the mail. In a further embodiment, the results may be transmitted in an encrypted or compressed form, depending on the security and speed of the network.

In still a further embodiment, the step of generating a medical data analysis including the PHI with processed results of the medical image may further include steps of recognizing and linking the identifier of the medical image with the patient's PHI, and combining the PHI with processed results of the medical image.

In another aspect, a data processing system may include a computing device, an anonymizing device, an image processing unit, and a processed results managing (PRM) unit. In one embodiment, the computing device, the anonymizing device and the PRM unit are located in a local site, and the image processing unit is located in a remote site.

In an exemplary embodiment, the computing device may receive a patient's medical information that may include the patient's protected health information (PHI) and at least one medical image, and the anonymizing device is configured to separate the patient's PHI 310 from the medical image, and keep the patient's PHI at the local site to minimize the risk of disclosing the PHI during data transmission.

The medical image is then transmitted from the data communicating unit at the local site to the data communicating unit at the remote site, and further transmitted to the image processing unit, which is configured to analyze the medical image and generate analyzed results. In one embodiment, the image processing unit is configured to assign an identifier to the analyzed results, so that the analyzed results can be matched with corresponding patient's PHI when transmitted back to the local site.

The analyzed results are then transmitted back to the local site, received by the data communicating unit, and further transmitted to the processed results managing (PRM) unit. The PRM unit is configured to recognize and link the analyzed results to the corresponding patient's PHI and combine them to generate a report.

DETAILED DESCRIPTION OF THE INVENTION

Figure 1:
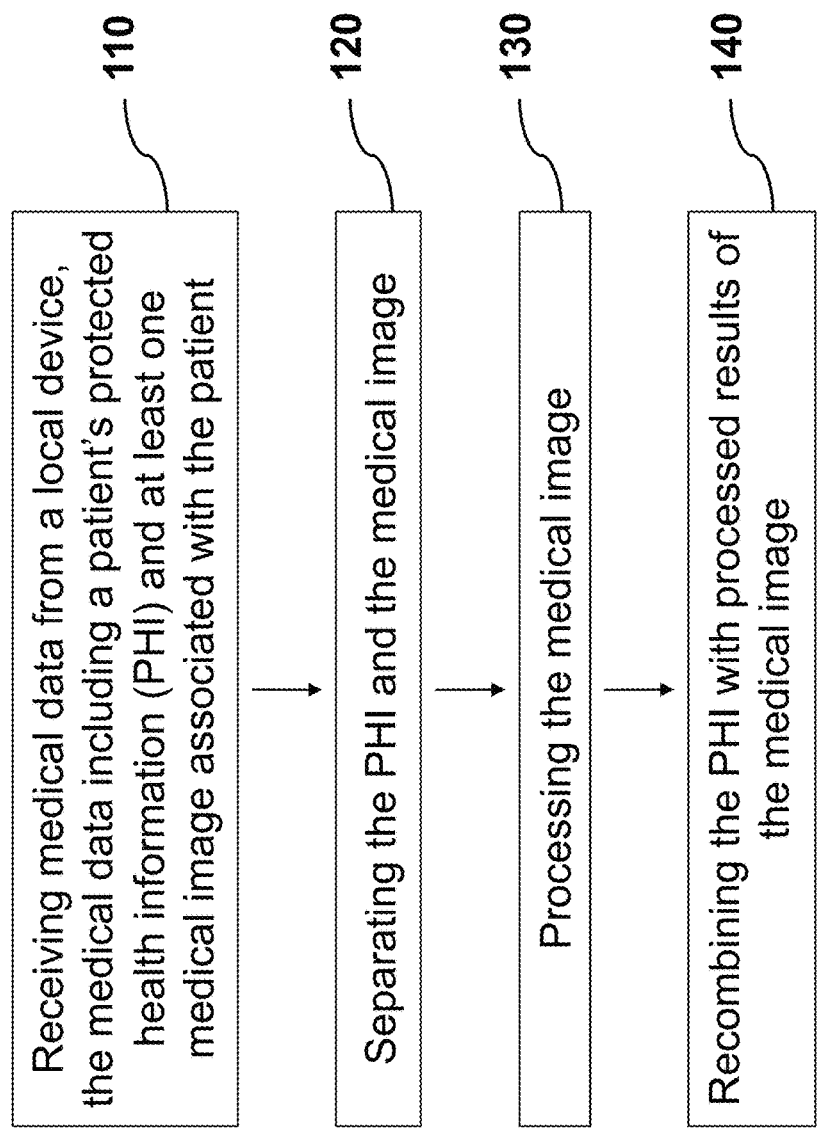
FIG. 1 illustrates a method for processing medical data in the present invention.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Patient medical images, such as those in the DICOM, RAW or TIFF format, typically contain a large amount of metadata which can be used to identify the patient, such as a name, identity, date, time, physician, etc. Computational medical image analysis, sometimes referred to as image processing, can provide much richer information than available from unprocessed images, for example reveal arterial blood flow, but may be impractical or undesirable to perform locally. The transfer of medical images involves risks of compromising patient confidentiality both during transport and while the data resides at the destination. These risks can be minimized by not transferring unnecessary Protected Health Information (PHI) or patient-identifying information with the images. Any such information could remain at the point of origin, which is presumably a secure location.

The present invention is related to an automated process wherein medical images are computationally processed at a remote location with minimal sharing of patient information. A remote location may refer to any location other than the origin of the images, such as "the cloud," or in some cases, it may simply be a separate room, building, or computer system where the image analysis is performed, that exists within a hospital or clinic where the images were acquired. Namely, the present invention is configured to automate the anonymization of images. The resulting data may be images or data which can be reconstructed into images, and does not necessarily consist of the complete information present in the original images, e.g. it may only consist of the information necessary to perform a particular analysis. In other words, there may be some "preprocessing" prior to transfer.

Patient-identifying metadata is typically present in the header of medical image files. Several methods of anonymization have been developed and are well known and commonly applied by individuals who perform research using medical data. Typical methods of anonymizing images include converting/re-encoding medical images to another file format which does not include metadata, blanking out or replacing identifying data in the image header, encrypting or masking the identifying data, among other approaches.

However, in some cases it may be desirable to not remove or redact all metadata present in the image file header. Certain information present in the metadata may not identify the patient, yet may be useful for the analysis to be performed. For example, characteristics of the imaging acquisition, such as frame rate and pixel size may be useful information for a computational analysis. In these cases, only the patient-identifying metadata may be deleted, or alternatively, if all metadata is removed, for example, if the file is anonymized by converting to a file format which does not include metadata, the metadata relevant for image analysis may be transferred for analysis in a separate file or other form to the remote location. In the present invention, we will still focus on an improved medical data processing system and method to analyze medical image data while minimizing the risk of compromising patient-identifying information.

In one aspect, a method for processing medical data may include steps of receiving medical data from a local device, the medical data including a patient's protected health information (PHI) and at least one medical image associated with the patient 110; separating the PHI and the medical image 120; processing the medical image 130; and generating a medical data analysis including the PHI with processed results of the medical image 140.

Figure 1A:
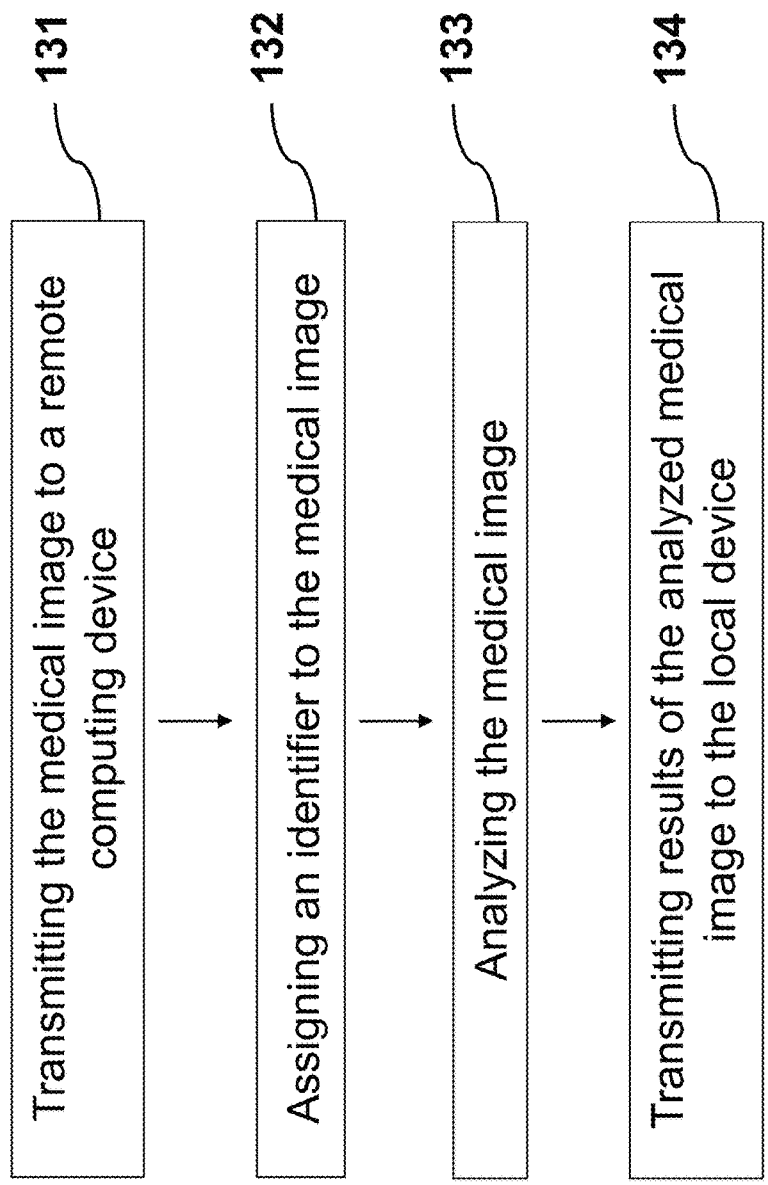
FIG. 1a illustrates one embodiment of the step of processing the medical image in the present invention.

In one embodiment, the step of separating the PHI and the medical image 120 can be conducted on the local device. In another embodiment, the step of processing the medical image 130 may further include steps of transmitting the medical image to a remote computing device 131; assigning an identifier to the medical image 132, analyzing the medical image 133 and transmitting results of the analyzed medical image to the local device 134 as shown in FIG. 1a. It is important to note that step 120 is the step of anonymization, which is performed prior to the medical images leaving the local device. This is necessary to prevent the exposure of PHI to a remote computer system. For example, if the medical images are being transferred from a hospital through the Internet, they should be anonymized before they leave the router or gateway that connects the hospital to the Internet. It does not need to occur immediately before the images are transferred beyond the hospital; the anonymization may be performed by different computers or network equipment, depending on the layout of the hospital's network. It is also noted that the image processing step can also be conducted in the local computing device.

In an exemplary embodiment, the medical image and results of the analyzed medical image can be transmitted electronically, such as through the Internet, a private network, or intranet in steps 131 and 134. However, in some cases, such as limited network connectivity, it may be preferable for the data to be transferred physically, such as a DVD or hard disk drive sent through the mail. In a further embodiment, the results may be transmitted in an encrypted or compressed form, depending on the security and speed of the network. The processed medical data are preferably transferred by a number of standard protocols across a network, such as through Hypertext Transfer Protocol (HTTP), File Transfer Protocol (FTP), or their secure variants (HTTPS, SFTP). It is also possible that a dedicated protocol specifically to transfer medical image data could be used. Data are received by a computer running appropriate software for the transfer protocol. For example, in some embodiments, a web server would receive the images and data. Customized HTTP headers would provide the server with additional information regarding the nature of the images and the analysis to be performed. The receiving computer might perform the image analysis itself, or it might further transfer the images and data to a computer dedicated for one or more analyses.

With anonymization, it is necessary to keep track of each patient/set of images by means which do not reveal the identity of the patient. This is necessary so that the results can properly be provided and interpreted for the correct patient. Coordinating communication between networked computers has been previously addressed in many different ways which could be used without utilizing or exposing patient-identifying data.

Figure 1B:
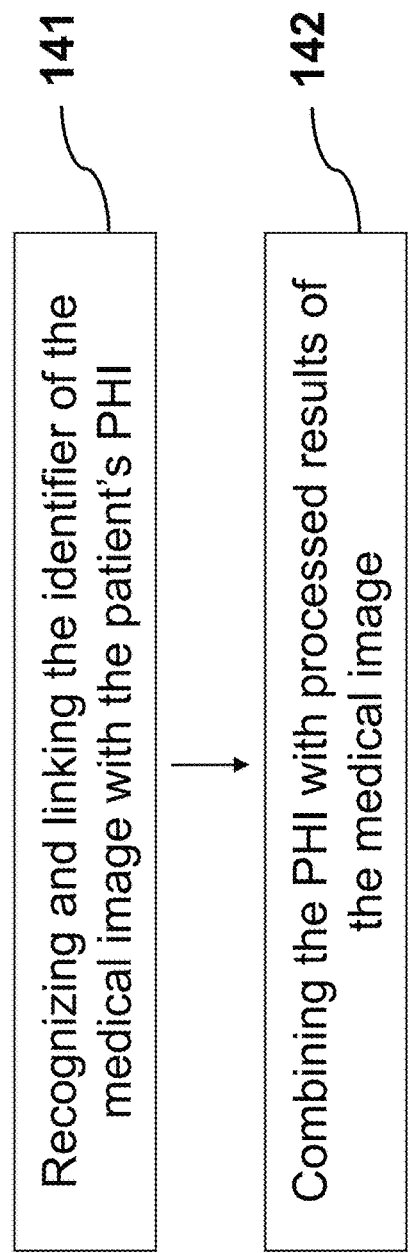
FIG. 1b illustrates one embodiment of the step generating a medical data analysis in the present invention.

In still a further embodiment, the step of generating a medical data analysis including the PHI with processed results of the medical image 140 may further include steps of recognizing and linking the identifier of the medical image with the patient's PHI 141, and combining the PHI with processed results of the medical image 142, as shown in FIG. 1b. The identifier in step 132 may be randomly generated in the local device or assigned by another computer system which handles a related task such scheduling of computer time or billing. In some embodiments, instead of generating a randomized identifier, a set of images and data could be kept track of based on the characteristics of the image transfer, such as the time at which images were sent/received. This could further be combined with information corresponding to the user or their organization, such as a user ID or customer ID, to uniquely identify the set of images while maintaining patient anonymity.

Depending on the type of analysis to be performed and the needs of the local user, in some cases it may be preferable to use a one-time identifier or a longer-term identifier, for example in the case of longitudinal data or multiple sets of images used for a particular analysis. In place of a single longer-term identifier, variations of an identifier composed of constant portion combined with a variable portion may be used for related image analyses. For example, for analysis of multiple image series acquired for a single patient, different identifiers composed of a constant sequence of characters (generated through random or other means) combined with variable times when image sets were submitted for analysis might be used to track the images.

In some embodiment, the identifier in step 132 may be stored in the local device, which can be done in multiple ways. In one embodiment, the identifier, along with the patient's PHI may be linked together and stored on the local computer, in memory or on a disk. The patient information does not necessarily need to be stored separately, and may instead be present in the original images or other images present on that local computer. In another embodiment, the local computer may not store the patient's PHI itself, and instead store an identifier link to a particular patient or set of images in a local patient data repository, for example a Picture Archiving and Communication System (PACS) or Radiology Information System (RIS). In a further embodiment, the identifier link may be stored on a local patient data repository, clinical database, or server, for example added as an entry to the patient record, which is advantageous because it would enable computers or devices other than the local computer which originally transferred the images to access the results. Namely, a different device which could access the database or server, could then read the identifier link and use it to transfer the results from the remote site. The device could additionally obtain patient information, possibly from the same database and use that to reassemble the results with PHI.

When the analysis is complete, results may be returned. They may either be transferred to the initial computer system or another secure device. This may either be "push" or "pull," meaning the transfer of results may be initiated at the analysis end or the retrieval device, respectively. In some cases, it will be preferable for results to not be retrieved immediately, and they will instead reside at the site of processing or another location for some duration. Results will not necessarily be retrieved in the order they were submitted, and it may be preferable to collect or transfer several sets of results at the same time, for example if many cases are being analyzed as part of a clinical study.

Figure 2:
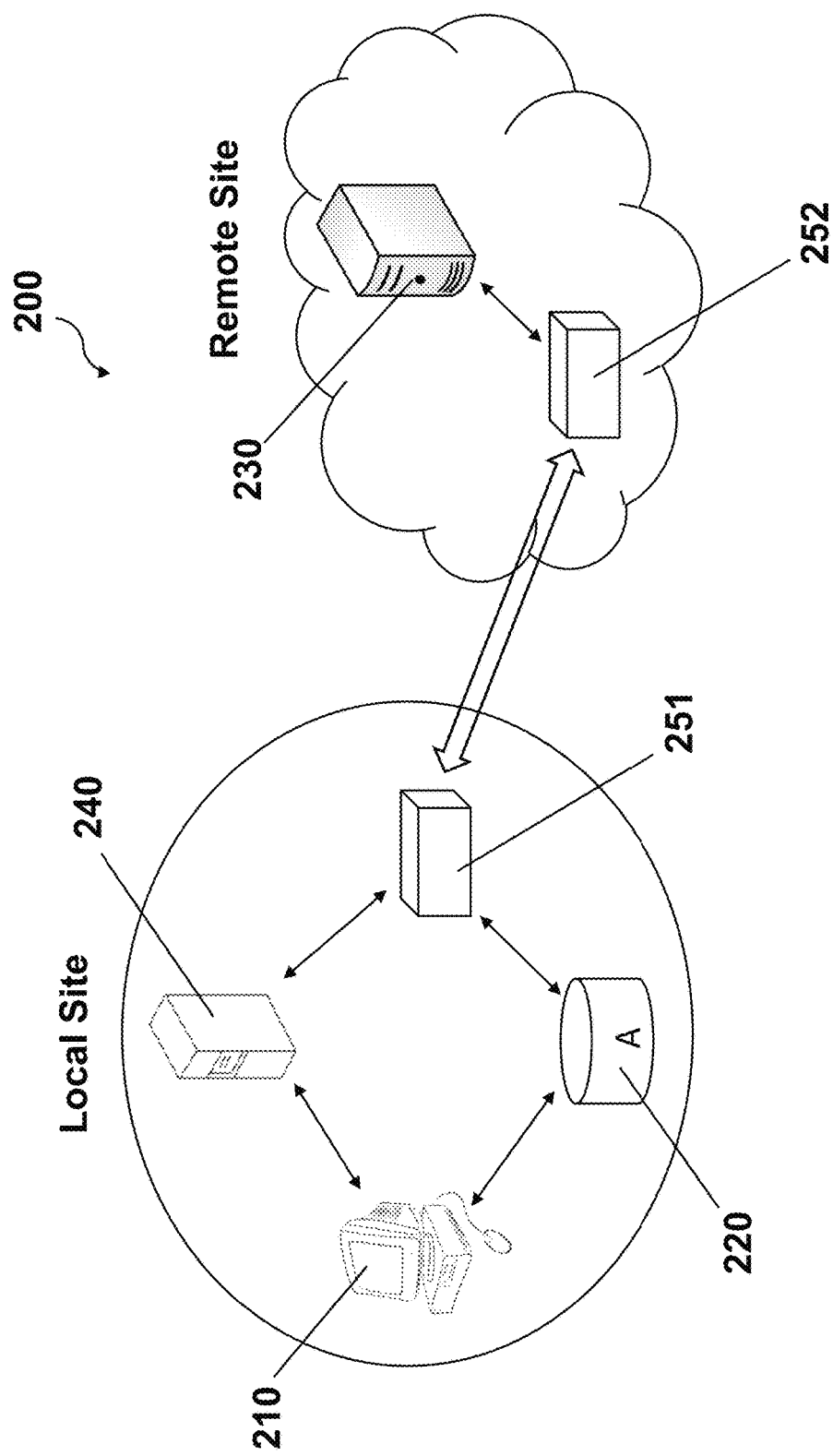
FIG. 2 illustrates a data processing system in the present invention.

In another aspect, a data processing system 200 may include a computing device 210, an anonymizing device 220, an image processing unit 230, and a processed results managing (PRM) unit 240. In one embodiment, the computing device 210, the anonymizing device 220 and the PRM unit 240 are located in a local site, and the image processing unit 230 is located in a remote site as shown in FIG. 2. Each of the local site and remote site may further include a data communicating unit 251 and 252 respectively to transmit the data from the local site to the remote site and vice versa.

Figure 3:
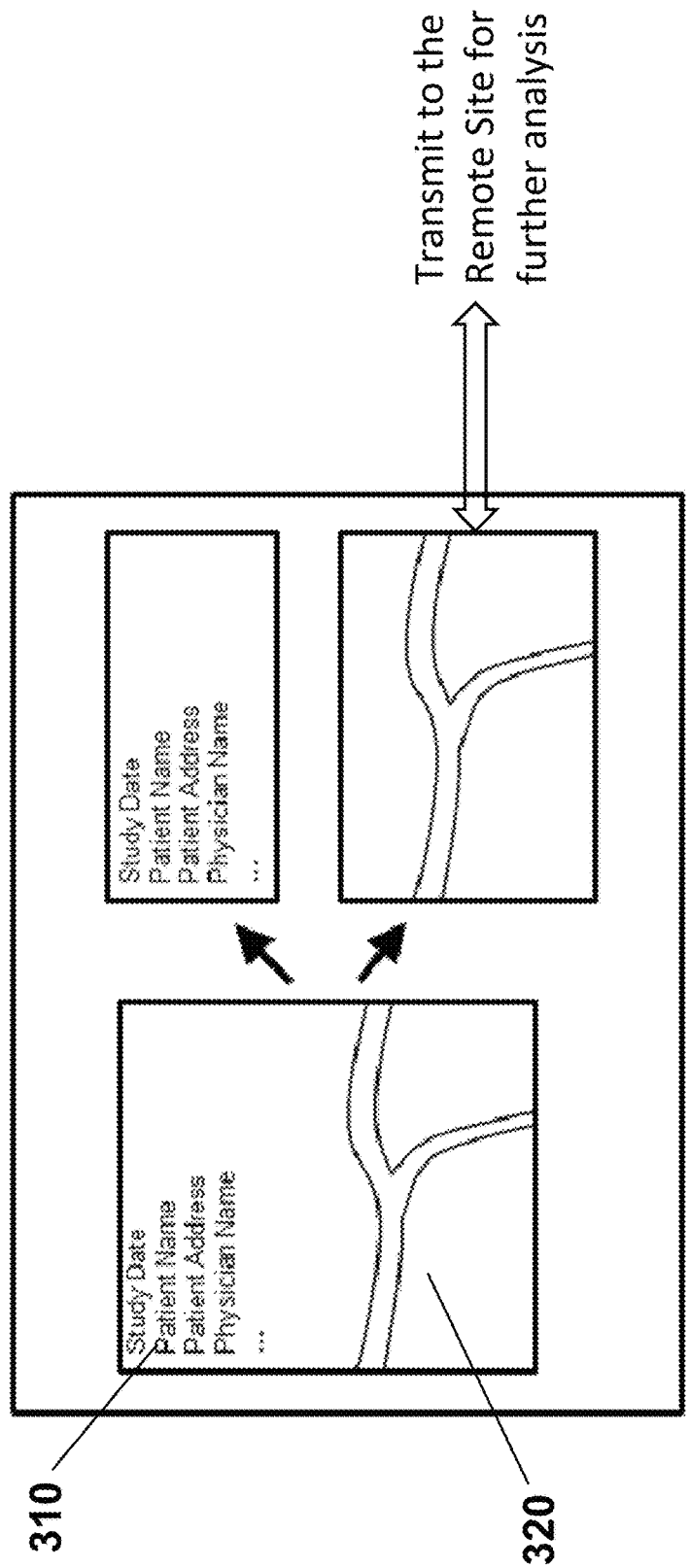
FIG. 3 illustrates a schematic view of separating the PHI from the medical image in the present invention.

In an exemplary embodiment, the computing device 210 may receive a patient's medical information that may include the patient's protected health information (PHI) 310 and at least one medical image 320, and the anonymizing device 220 is configured to separate the patient's PHI 310 from the medical image 320 as shown in FIG. 3, and keep the patient's PHI 310 at the local site to minimize the risk of disclosing the PHI 310 during data transmission.

Figure 3A:
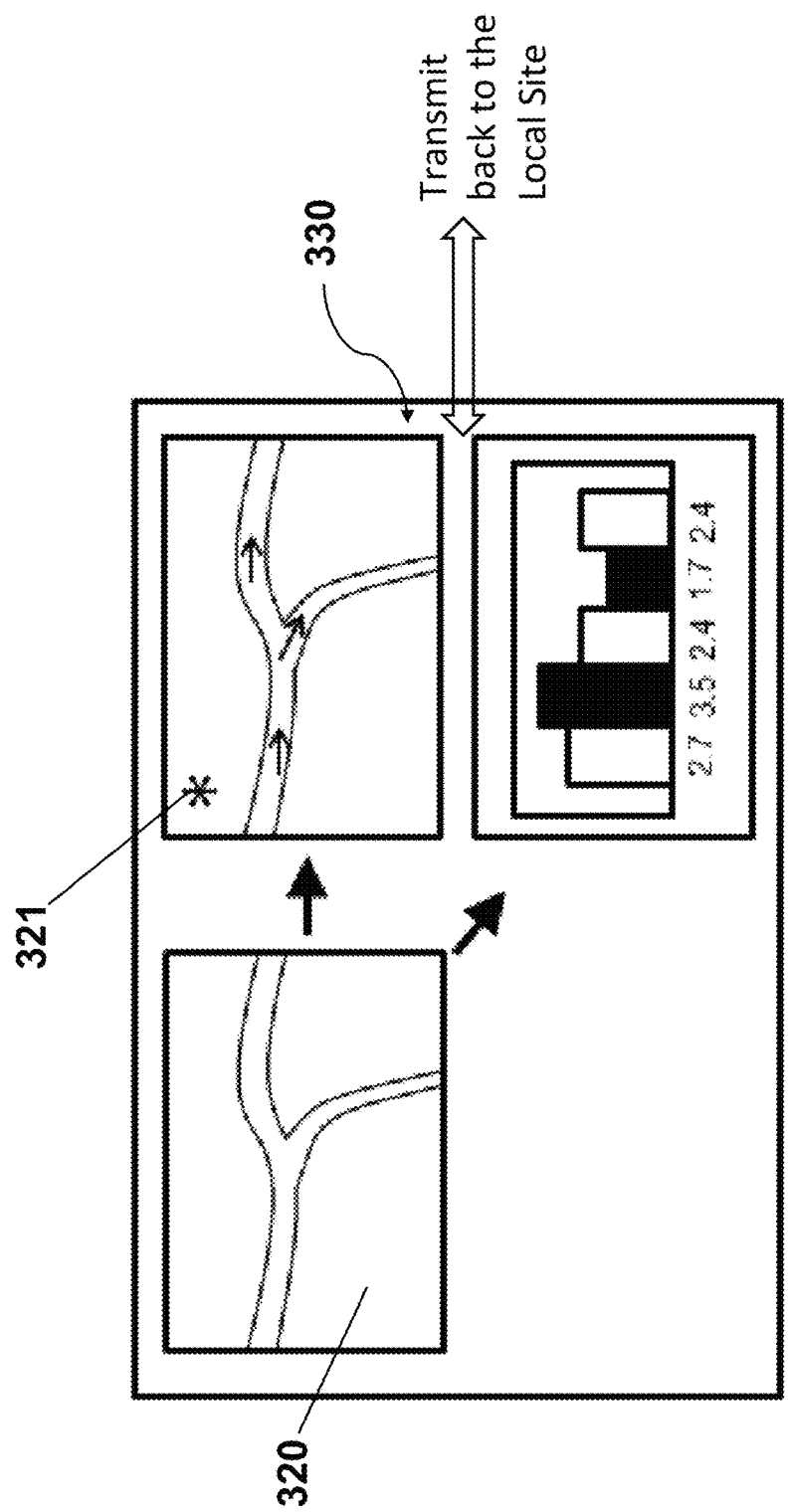
FIG. 3a illustrates a schematic view of processing the medical image data in the present invention.

The medical image 320 is then transmitted from the data communicating unit 251 at the local site to the data communicating unit 252 at the remote site, and further transmitted to the image processing unit 230, which is configured to analyze the medical image 320 and generate analyzed results 330 as shown in FIG. 3*a*. In one embodiment, the image processing unit 230 is configured to assign an identifier 321 to the analyzed results 330, so that the analyzed results 330 can be matched with corresponding patient's PHI when transmitted back to the local site.

Figure 3B:
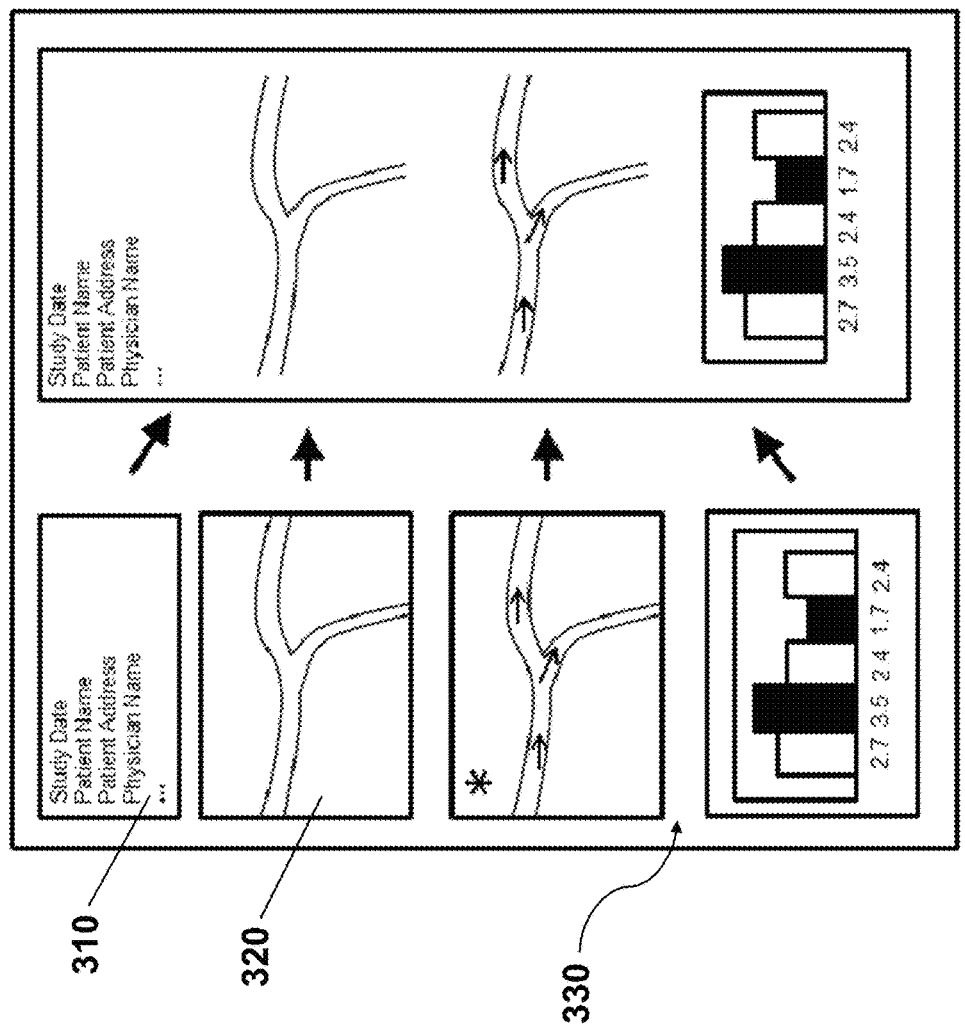
FIG. 3b illustrates a schematic view of generating a medical data analysis by combining the patient's PHI with the analyzed results in the present invention.

The analyzed results 330 are then transmitted back to the local site, received by the data communicating unit 251, and further transmitted to the processed results managing (PRM) unit 240. The PRM unit 240 is configured to recognize and link the analyzed results 330 to the corresponding patient's PHI 310 and combine them to generate a report as shown in FIG. 3*b*. More specifically, the PRM unit 240 is configured to recognize the identifier 321 and link the analyzed results 330 with the corresponding patient's PHI 310.

Figure 4:
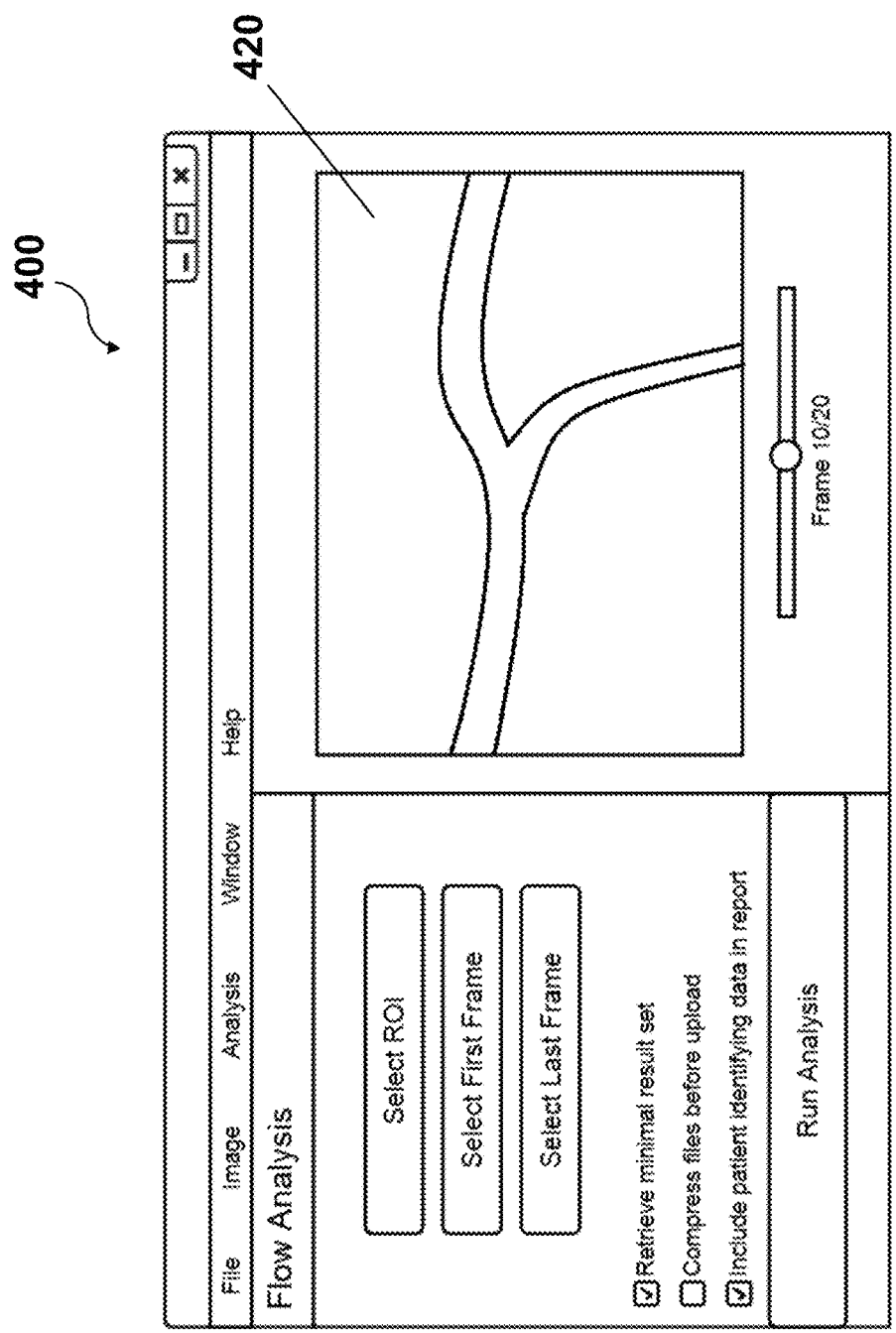
FIGS. 4 and 4a illustrate schematic view of graphical user interface of the medical data processing system in the present invention.
Figure 4A:
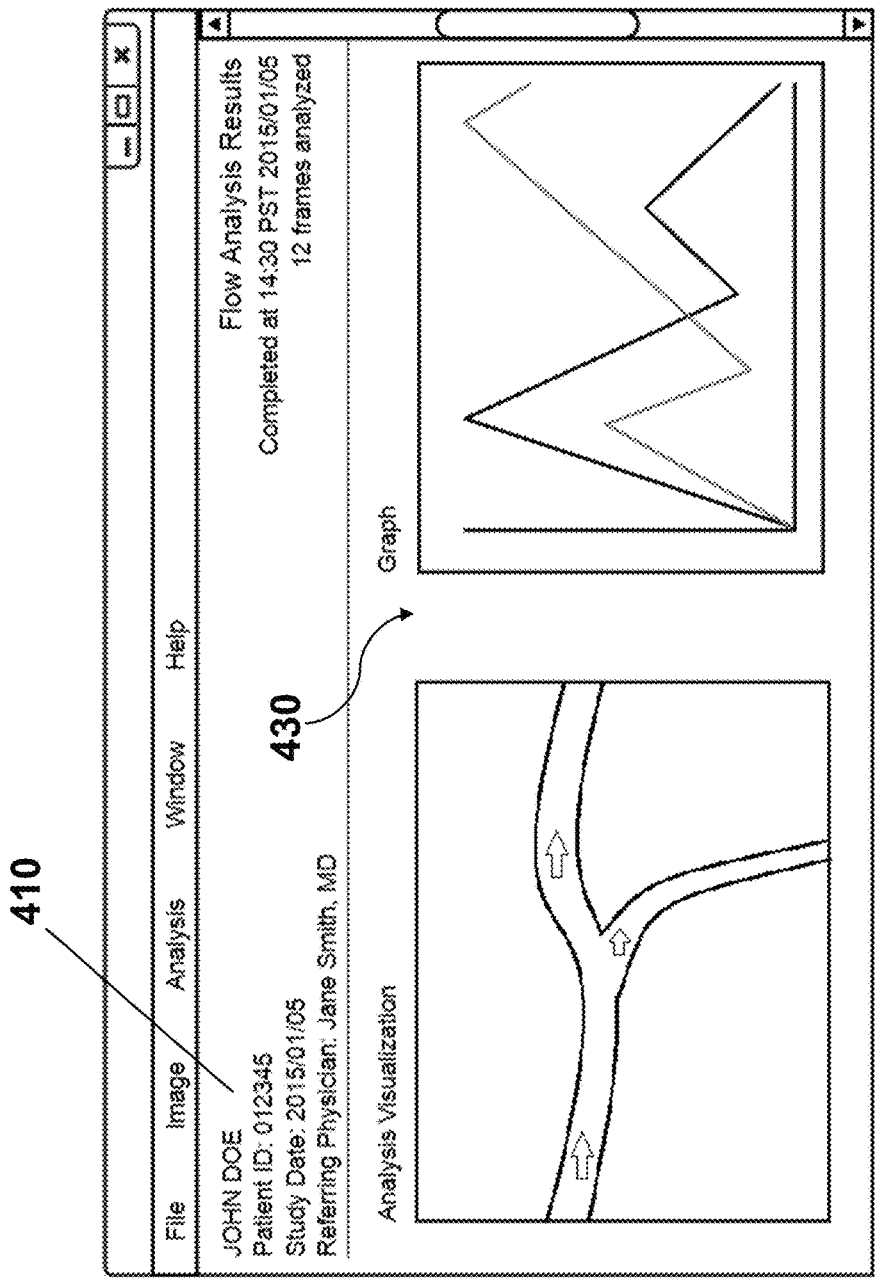

FIGS. 4 and 4*a* illustrates screenshots of a graphical user interface (GUI) 400 of the medical data processing system in the present invention. In one embodiment, the GUI 400 may be shown on the computing device 210 at the local site. At the present stage, the metadata of the patient's PHI (not shown in FIG. 4) is still together with the medical image 420. When all parameters of the medical analysis are set, a button "Run Analysis" can be pressed to start the medical analysis. The analysis may begin with separating the patient's PHI (not shown in FIG. 4) from the medical image 420, which can be conducted by the anonymizing device 220. In one embodiment, the metadata of the patient's PHI is kept in the local site, and the medical image 420 can be transmitted to the remote site for further analysis as shown in FIGS. 2 and 3*a*.

The medical image 420 can be analyzed by the image processing unit 230 and the analyzed results 430 can be transmitted back to the local site. When receiving the analyzed results 430, the processed results managing (PRM) unit 240 is configured to combine the patient's PHI 410 with the analyzed results 430 as shown in FIG. 4*a*.

The image analysis results and PHI may be recombined in the form of a rich image format, such as DICOM (images and headers), or the images and PHI may appear alongside each other in a report, or the PHI may be superimposed or incorporated into the image itself, among other methods. The recombination allows the creation of a report which combines the image analysis results with other data or images and patient-identifying information. This report may either be prepared remotely and returned with the image analysis results, with the receiving device filling in the missing patient-identifying information, or the report may instead be prepared on the receiving device itself by the client software. In a preferred embodiment, the client software stores report templates applicable to various analyses and combines downloaded images and data with PHI present on the device or accessible to the device (such as a local PACS) to generate a complete report. This simplifies the process for a user evaluating image analysis results.

The retrieval and recombination of data may be done on devices or at locations other than the original sender, provided they have the correct identifier or other means to request and recombine the results with the patient-identifying information, such as access to a server or database with this information. Which individuals or computers are allowed to access the results may be determined at the time when the images are submitted for analysis, or at a later point, such as by sharing the unique identifier corresponding to the image set. If the results are being retrieved on a computer or device other than the one which initially sent the images, it may, for example access the necessary PHI from a local PACS, RIS, or other repository of patient data. The client software on that device might then recombine the results with the patient-identifying data.

Having described the invention by the description and illustrations above, it should be understood that these are exemplary of the invention and are not to be considered as limiting. Accordingly, the invention is not to be considered as limited by the foregoing description, but includes any equivalent.

What is claimed is:

1. A computer-implemented method for processing medical data comprising steps of:
   receiving medical data from a local device, the medical data including a patient's protected health information (PHI) and at least one medical image associated with the patient;
   separating the PHI and the medical image;
   processing the medical image; and
   combining the PHI with processed results of the medical image,
   wherein the step of processing the medical image includes steps of transmitting the medical image to a remote computing device, assigning an identifier to the medical image, analyzing the medical image, and transmitting results of the analyzed medical image to the local device, and
   wherein the step of combining the PHI with processed results of the medical image includes a step of recognizing and linking the identifier of the medical image with the patient's PHI.

2. The computer-implemented method for processing medical data of claim 1, wherein the step of separating the PHI and the medical image is conducted on the local device.

3. The computer-implemented method for processing medical data of claim 1, wherein the identifier is allowed to be generated on the local device.

4. The computer-implemented method for processing medical data of claim 1, wherein the results of the analyzed medical image are transmitted electronically, such as through the Internet, a private network, or intranet.

5. A data processing system comprising:
   a local computing device to receive medical data including a patient's protected health information (PHI) and at least one medical image associated with the patient;
   an anonymizing device to separate the PHI with the medical image;
   an image processing unit to analyze the medical image; and
   a processed results managing (PRM) unit configured to recognize and link analyzed results of the medical image to the corresponding patient's PHI, and combine the analyzed results and the patient's PHI to generate an analysis report,
   wherein the image processing unit is configured to assign an identifier to the analyzed results, so that the analyzed results are matched with corresponding patient's PHI at the local computing device, and
   wherein the PRM unit is configured to recognize the identifier and link the analyzed results with the corresponding patient's PHI.

6. The data processing system of claim 5, wherein the computing device, the anonymizing device and the PRM unit are located in a local site, while the image processing unit is located in a remote site.

7. The data processing system of claim 5, wherein each of the local site and remote site further includes a data communicating unit to transmit the data from the local site to the remote site and vice versa.

8. The data processing system of claim 6, wherein the patient's PHI is kept at the local site.

* * * * *